United States Patent [19]

Otani et al.

[11] 4,423,218

[45] * Dec. 27, 1983

[54] ANTIBIOTIC NEPLANOCIN A

[75] Inventors: Masaru Otani; Satoshi Yaginuma; Masatoshi Tsujino; Naoki Muto; Tetsu Saito, all of Shizuoka; Tadashiro Fujii, Mishima, all of Japan

[73] Assignee: Toyo Jozo Kabushiki Kaisha, Shizuoka, Japan

[*] Notice: The portion of the term of this patent subsequent to Mar. 23, 1999, has been disclaimed.

[21] Appl. No.: 205,350

[22] Filed: Nov. 3, 1980

Related U.S. Application Data

[63] Continuation of Ser. No. 18,790, Mar. 8, 1979, abandoned.

[30] Foreign Application Priority Data

May 25, 1978 [JP] Japan .................................. 53-62899
Aug. 10, 1978 [JP] Japan .................................. 53-98027
Jan. 29, 1979 [JP] Japan .................................. 54-8295

[51] Int. Cl.³ .......................................... C07D 473/32
[52] U.S. Cl. ................................... 544/277; 424/253
[58] Field of Search ........................ 424/253; 544/277

[56] References Cited

U.S. PATENT DOCUMENTS 4,138,562  2/1979  Vince ............................. 424/253
4,321,376  3/1982  Otani et al. ..................... 424/253

Primary Examiner—Nicholas S. Rizzo
Attorney, Agent, or Firm—Young & Thompson

[57] ABSTRACT

Antibiotic neplanocin A of the formula

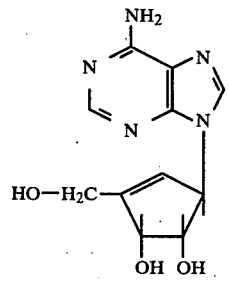

is produced by culturing *Ampullariella* sp. A 11079 FERM-P No. 4494 in a nutrient medium and then separating the neplanocin A thus produced from the culture medium.

1 Claim, 4 Drawing Figures

ANTIBIOTIC NEPLANOCIN A

This is a continuation, of application Ser. No. 18,790, filed Mar. 8, 1979 now abandoned.

The present invention relates to a novel antibiotic neplanocin having inhibitory activity on plant pathogenic microorganisms.

Neplanocin A is a weakly basic substance and has the following physico-chemical properties:

(1) Elementary analysis: Found: C: 49.96%, H: 5.00%, N: 26.43%: Calculated: C: 50.19%, H: 4.97%, N: 26.60%.

(2) Molecular weight (calculated from mass spectrum analysis): 263

(3) Molecular formula: $C_{11}H_{13}N_5O_3$ (4) Melting point (determined by thermal analysis): 216° C.

(5) Specific rotation: $[\alpha]_D^{20} = -157°$ (C=0.45%, $H_2O$)

(6) Ultraviolet absorption spectrum: (14 γ/ml) in $H_2O$: shown in FIG. 1

$\lambda max = 263$ mμ, $E_{1\ cm}^{1\%} = 602.1$ at pH 3:

$\lambda max = 261$ mμ, $E_{1\ cm}^{1\%} = 566.4$ at pH10:

$\lambda max = 263$ mμ, $E_{1\ cm}^{1\%} = 595.0$ (7) Infrared absorption spectrum (KBr): shown in FIG. 2

Absorption bands at 3360, 3200, 2920, 1640, 1600, 1570, 1480, 1415, 1370, 1330, 1300, 1250, 1205, 1160, 1115, 1080, 1050, 1005, 910, 850, 790, 730 $cm^{-1}$.

(8) Nuclear magnetic resonance spectrum: shown in FIG. 3 (internal standard DSS, in Deuterium dimethylsulfoxide, 100 MHz).

(9) Solubility:

Soluble: water, dimethylsulfoxide, dimethylformamide, acetic acid and aqueous acetone.

Insoluble: ethyl acetate, chloroform, benzene, hexane.

(10) Color reactions:

Positive: decolorization of potassium permanganate, periodate oxidation and anisaldehyde.

Negative: ferric chloride, ninhydrin, anilinephthalate, Molisch and Fehling.

(11) Nature: weakly basic.

(12) Color: white.

(13) Rf value (silica gel, Tokyo Kasei Co., silica gel f):

n-butanol:acetic acid:water (6:1:1); Rf=0.36 n-butanol:conc. aq. ammonia:water (10:0.5:2); Rf=0.27 n-propanol:conc. aq. ammonia:water (10:1:1); Rf=0.41 acetone:water (10:1); Rf=0.34 ethyl acetate:methanol:water (10:2:1); Rf=0.21 chloroform:methanol:acetic acid (10:2:1); Rf=0.17

(14) Chemical structure

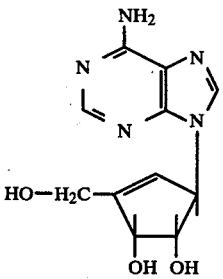

The biological properties of neplanocin A are as follows:

(1) Growth inhibitory activity on plant pathogenic fungi:

100 γ/ml solution of neplanocin A on an agar plate of *Helminthosporium oryzae* M 0306 shows the inhibitory zone of 18.9 mm in diameter.

(2) Acute toxicity:

$LD_{50}$: 13.7 mg/kg (i.p., mice)

No mortalities were observed when administered intraperitoneally for 14 days, 5 mg/kg/day.

Neplanocin A can be used in a form of a physiologically acceptable salt of a mineral acid or organic acid such as the hydrochloride, acetate, tartrate, citrate or succinate.

A neplanocin-producing microorganism was isolated from a soil collected in an onion field of Niigata-ken, Japan and belongs to genus Ampullariella. The strain is referred to as Ampullariella sp. A 11079 and has been deposited for permanent collection at the Institute for Microbial Industry and Technology, Japan as FERM-P No. 4494.

Ampullariella sp. A 11079 FERM-P No. 4494 has the following taxonomic characteristics:

(I) Morphological characteristics:

Observations on inorganic salts-starch agar medium at 30° C. for 10–15 days culture were as follows:

Strain A 11079 produces a curved and branching substrate mycelium, 0.5–0.8μ in diameter and a slightly unmatured aerial mycelium.

Sporangiophore grown on substrate mycelium has sporangia and shapes of sporangium are cylindrical or bottle-shaped and measure from 5–15×10–25μ. Many sporangiospores are arranged in parallel chains within the sporangium. Sporangiospores are motile by a tuft of polar flagella in water and are rod-shaped measuring from 0.5–1.0×1.0–2.0μ.

(II) Composition of diaminopimelic acid:

Diaminopimelic acid detected by whole cell analysis is of the meso- and hydroxy-type.

(III) Culture characteristics on various media:

Observations of culture characteristics on various media at 30° C. for 20 days culture are shown in Table 1. No aerial mycelium was observed except slight formation of unmatured growth aerial mycelia on inorganic salts-starch agar medium and oatmeal agar medium.

Indication of color is based on the indication in "Color Harmony Manual", 4th Ed., 1958, published by Container Corporation of America.

(IV) Physiological properties:

Physiological properties are illustrated as follows:

(1) Utility of carbon sources:

| Carbon source | utilization | Carbon source | utilization |
|---|---|---|---|
| L-arabinose | + | salicin | + |
| D-xylose | + | D-galactose | + |
| D-glucose | + | glycerol | + |
| D-fructose | + | L-sorbose | − |
| D-mannose | + | trehalose | + |
| D-mannitol | + | α-melibiose | − |
| inositol | − | D-ribose | − |
| L-rhamnose | + | maltose | + |
| sucrose | + | melezitose | − |
| β-lactose | − | D-cellobiose | + |
| raffinose | − | D-sorbitol | − |
| cellulose | − | dulcitol | − |
| starch | + | | |

(+: positive, −: negative)

TABLE 1

Cultural characteristics on various media:

| Medium | Growth | Sporangium | color of substrate mycelium | soluble pigment |
|---|---|---|---|---|
| Sucrose-nitrate agar | poor to medium | few | pearl pink(3ca)-light melon yellow(3ea) | none |
| Glucose-asparagine agar | medium to poor | few | bamboo(2fb)-pearl pink(3ca) | none |
| Glycerol-asparagine agar | poor to medium | none | bamboo(2fb)-pearl pink(3ca) | none |
| Inorganic salts starch agar | good to medium | good | amber(3lc)-pastel orange(4ic) | none |
| Tyrosine agar | poor to medium | none | light amber(3ic) | |
| oatmeal agar | good | medium | amber(3lc)-bright maize(3la) | none |
| Yeast-malt agar | good to medium, slight wrinkles | poor | topaz(3ne)-amber(3pe) | pale amber(3pe) |
| Glucose-yeast extract agar (Waksman medium No. 28)* | medium to good | none | cinnamon(3le) | golden brown(3pg-3pi) |
| Glycerol-nitrate agar (Waksman medium No. 1)* | medium | none | colorless-bamboo(2fb) | none |
| Glucose-nitrate agar (Waksman medium No. 1)* | poor medium | none | colorless-bamboo(2fb) | none |
| Nutrient agar | poor | none | light amber(3ic)-cinnamon(3le) | golden brown(3pg) |
| Emerson's agar (Waksman medium No. 28)* | good to medium | none | cinnamon(3le)-camel(3ie) | golden brown (3pg-3pi) |
| Bennett's agar (Waksman medium No. 30)* | good to medium | none | amber(3pe)-topaz(3ne) | pale golden brown (3pg) |
| Peptone Czapeck's agar | medium to good | few | light amber(3ic)-amber(3lc) | pale golden brown (3pg) |
| Yeast extract Czapeck's agar | medium to good | few | amber(3lc-3nc) | none |
| Tyrosine agar**** | poor | none | light tan(3gc)-bisque(3ec) | clove brown(3pl) |
| Peptone-yeast iron agar | medium to poor | none | light amber(3ic) | dark spice brown (4pl) |
| Caseine agar**** | good | none | camel(3ie)-cinnamon(3le) | clove brown(3pl) |

*Waksman, S. A., "The Actinomycetes" Vol. 2, 1961, p. 327–334, Williams & Wilkins Co.
**J. Elisha Mitchell, Sci. Soc., 79, 54 (1963).
***J. Virol., 3, 210 (1969).
****J. Bacteriol., 69, 147 (1955).

(2) Growth temperature: 10°–45° C.
(3) Action on skim milk: peptonization and coagulation positives.
(4) Melanin production: Tyrosine agar medium; negative. Peptone yeast iron agar medium; positive.
(5) Starch hydrolysis: positive.
(6) Cellulose hydrolysis: negative.
(7) Casein hydrolysis: positive.
(8) Gelatin liquefaction: positive.
(9) Tyrosine decomposition: negative.
(10) Xanthine decomposition: negative.
(11) Hypoxanthine decomposition: negative.
(12) $H_2S$ formation: negative.
(13) Nitrate reduction: negative.

According to the above taxonomical data wherein the strain A 11079 has sporangia bearing sporangiophore grown on branching substrate mycelium, cylindrical or bottle-shaped sporangium, sporangiospores arranged in parallel chains within the sporangium, rod-shaped sporangiospore with tufty polar flagellum and meso diaminopimelic acid, this strain belongs to genus Ampullariella by consulting key to the genera of family Actinoplanaceae in Bergey's Manual of Determinative Bacteriology, 8th Ed., 1974, p. 707–708. Therefore this strain is referred to as Ampullariella sp. A 11079.

It is an object of the present invention to provide the novel antibiotic neplanocin A and derivatives thereof.

The present invention will now be described in more detail with reference to the accompanying drawings, in which.

Figure 1:
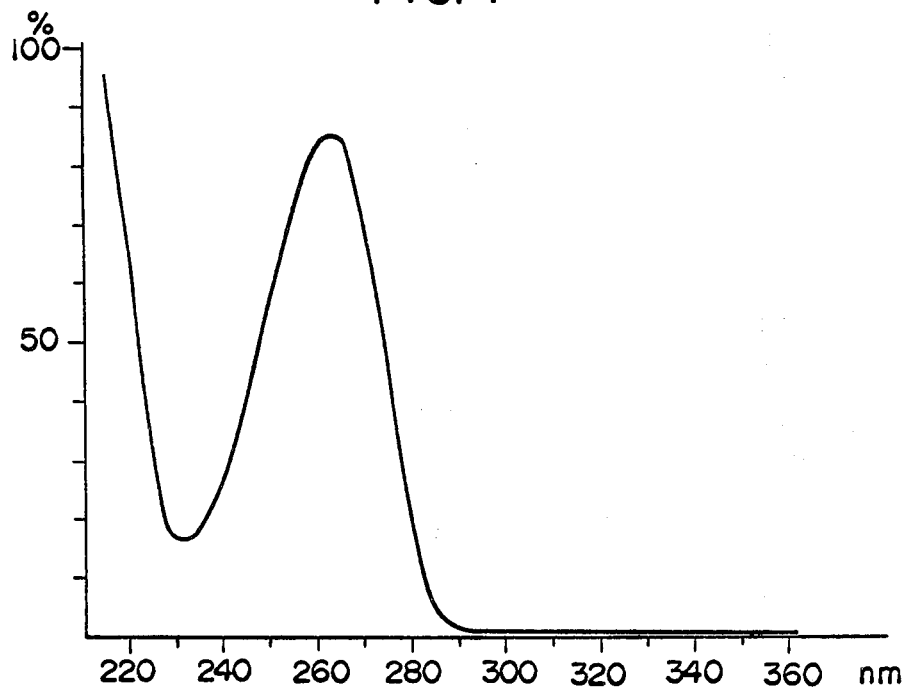
FIG. 1 is the ultraviolet absorption spectrum of neplanocin A.
Figure 2:
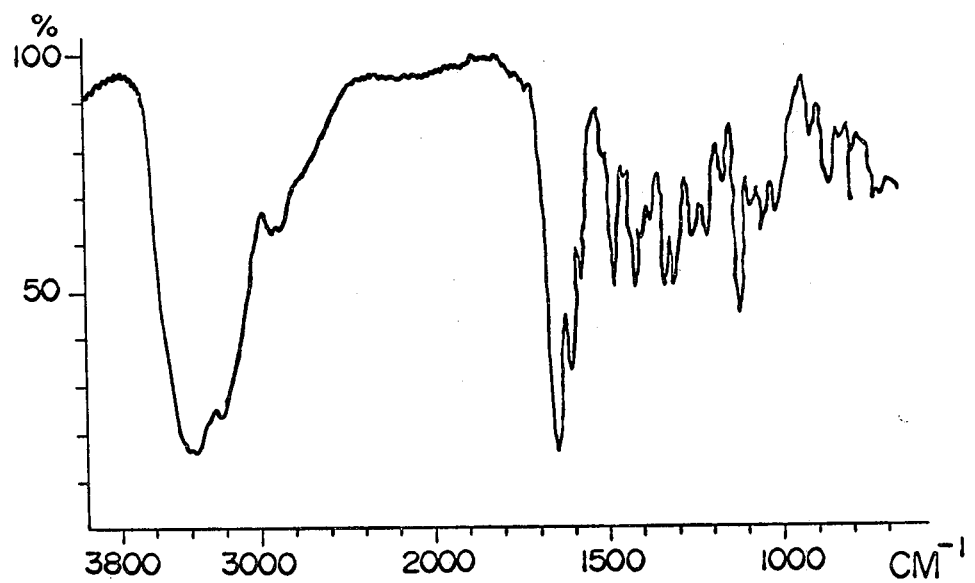
FIG. 2 is the infrared absorption spectrum of neplanocin A.
Figure 3:
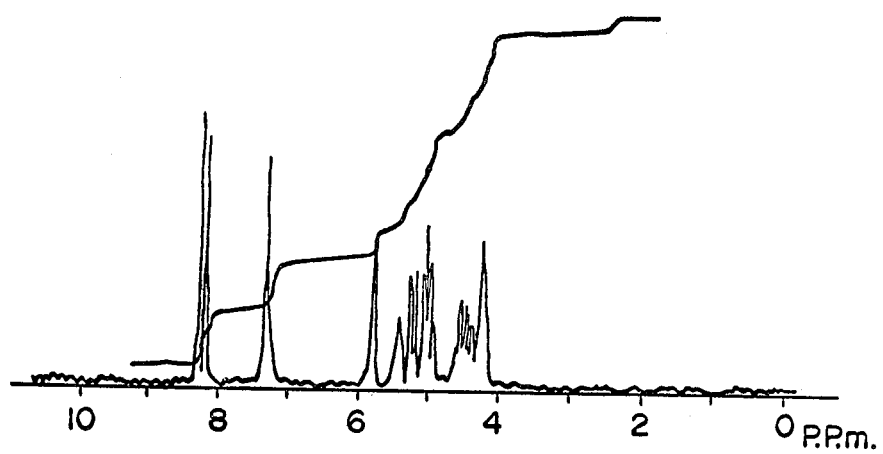
FIG. 3 is the NMR spectrum of neplanocin A.
Figure 4:
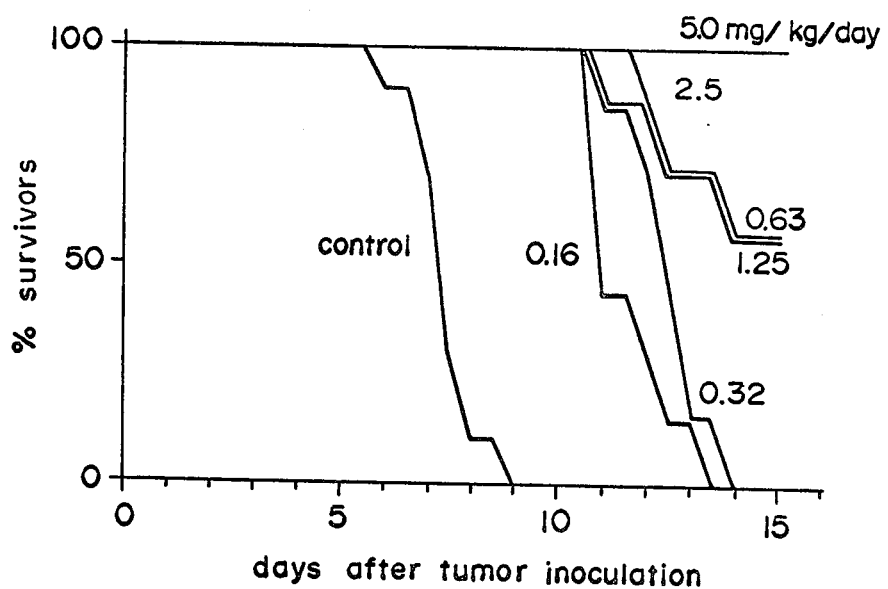
FIG. 4 shows the effect of neplanocin A on L-1210-leukemia-bearing mice.

Neplanocin A is produced, for example, by inoculating a strain Ampullariella sp. A 11079 FERM-P No. 4494 into a suitable nutrient medium. The cultivation of the microorganism can be carried out in a number of different ways, such as in a synthetic media or natural media, liquid or solid culture. For industrial production, liquid media are preferable. For the medium, there may be used assimilable carbon sources, nitrogen sources, inorganic salts and other media for antibiotic neplanocins-producing microorganisms. Examples of carbon sources are glucose, sucrose, glycerin, soluble starch, molasses and the like. Assimilable nitrogen sources such as peptone, corn steep liquor, soybean powder, meat extract, rice bran, casein hydrolysate, nitrate, ammonium salt and the like are used. An inorganic salt such as sodium chloride, phosphate (calcium, magnesium, ferrous or manganese) can also be used. Anti-foaming agents such as silicone oils or soybean oil can be added.

For liquid culture, submerged aeration culture may preferably be used. In this case the cultivating temperature will be selected for optimum temperature for microorganisms, and preferably is 25°–30° C. Cultivation time may depend on the conditions and generally may be 2-4 days. The pH of the medium during cultivation is preferably controlled to be neutral or slightly acidic.

The thus-cultured medium contains antibiotic neplanocins. Isolation of the antibiotic enplanocins can be performed by conventional isolation or separation processes for microorganism metabolites. Since neplanocins are weakly basic substances, they can be isolated by adsorption on suitable adsorbents followed by elution with suitable solvents. Examples of adsorbents are active carbon, cation exchange resin, active alumina or silica gel. Eluting solvents can be selected according to the adsorbent used, for example, water-miscible organic solvents such as aqueous methanol, aqueous acetone or aqueous dioxane or acidic, alkaline or salt solutions.

Further, the neplanocins can be isolated and purified on the basis of the weakly basic nature of the substances. For example, the antibiotics are adsorbed on cation exchange resin such as Amberlite IRC-50 (trademark of Rohm and Haas Co., U.S.A.) or Dowex 50 (trademark of Dow Chemical Co., U.S.A.) and are eluted with suitable acidic, alkaline or salt solutions.

A combination of adsorbent and ion exchange resin can preferably be applied for isolation, elution and purification of the antibiotics. For example, culture filtrate is charged on cation exchange resin Amberlite IR-120 (trademark) to adsorb the antibiotics, eluted with an alkaline solution such as 3.7 N aqueous ammonia to obtain the active fraction, and after the pH thereof is adjusted to neutral or weakly alkaline pH, the antibiotics are adsorbed on active carbon followed by elution with 70% methanol. The eluent is adsorbed on anion exchange resin Amberlite IRA-410 (trademark) and again eluted with water to collect the active fractions. The combined fractions are concentrated to obtain crude material and finally purified by silica gel adsorption chromatography. Further purification is performed by recrystallization. Purity as a single substance can be checked by showing a single melting point or a single spot on paper chromatography, thin layer chromatography and paper electrophoresis at 263 m$\mu$ ultraviolet light.

The following examples illustrate the present invention but are not to be construed as limiting:

EXAMPLE 1

100 ml. of aqueous medium (pH 6.5) containing glucose 2%, starch 2%, yeast extract 1%, casein hydrolysate 1% and calcium carbonate 0.2% were introduced in a 500 ml flask and sterilized at 120° C. for 15 minutes. Into two flasks of this medium, one loopful of slant culture of Ampullariella sp. A 11079 FERM-P No. 4494 was inoculated and shake cultured at 30° C. After four days, the cultured medium was transferred to 20 l. of the same sterilized medium hereinabove in a 30 l. jar fermenter and cultured at 30° C., with agitation at 300 r.p.m. and aeration of 20 l./min. for 48 hours.

The thus-cultured medium was transferred into 200 l. of aqueous medium (pH 6.5) containing glucose 4%, soybean powder 1%, meat extract 0.4%, peptone 0.4%, yeast extract 0.1%, NaCl 0.25% and calcium carbonate 0.1% and cultured at 30° C., with agitation at 180 r.p.m., and aeration 130 l./min., for 40 hours. The obtained cultured broth (about 200 l.) was filtered and the mycelia was washed with water. The filtrate and wash water were combined to obtain about 140 l. of clear filtrate (potency 57 mcg/ml as neplanocin A).

EXAMPLE 2

The filtrate obtained in Example 1 was passed through a column of 20 l. of cation exchange resin Amberlite IR-120 (trademark) (H$^+$ type) to absorb the material and washed with 100 l. of water. Elution was carried out with 3.7 N aqueous ammonia and the primary eluate (30 l.) was discarded. 90 l. of the following eluate were collected, adjusted to pH 8 by adding 6 N HCl, then passed through 4 l. of active carbon in a column, washed with water, thereafter eluted with 90 l. of 70% methanol solution. The thus-obtained eluate was concentrated under reduced pressure to give 1.5 l. of a concentrate. The concentrate was charged on a column of 10 l. of Amberlite IRA-410 (trademark) (OH$^-$ type) and eluted with water. The eluate was concentrated in vacuo, and the material was precipitated under cooling and filtered to obtain 41.8 g of crude neplanocin A (purity about 12%).

The crude neplanocin A (41.8 g) was dissolved in a small amount of water and charged on 2 l. of silica gel in a column (8.3×40 cm) packed with a solvent mixture of n-butanol: 28% aqueous ammonia:water (10:0.2:1), and thereafter eluted with the same solvent mixture.

Each 150 ml of the eluate was fractionated and active fractions were found in fractions Nos. 24–52. The said active fractions were collected, concentrated in vacuo, and allowed to stand under cooling.

The precipitate was collected by filtration to obtain 2.6 g of crude crystalline neplanocin A (yield 32%).

The crude neplanocin A was dissolved in about 60 ml of hot water and allowed to stand at room temperature. The precipitated white needle crystals were collected by filtration to obtain 2.01 g of crystalline neplanocin A (yield 25.2%).

What is claimed is:
1. Antibiotic neplanocin A of the formula

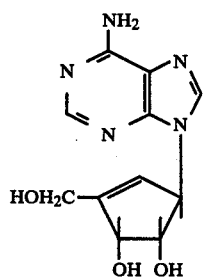

or a pharmaceutically acceptable salt thereof.

* * * * *